(12) United States Patent  
Tu et al.

(10) Patent No.: US 9,403,962 B2  
(45) Date of Patent: *Aug. 2, 2016

(54) ELASTOMER COMPOSITIONS WITH SILANE FUNCTIONALIZED SILICA AS REINFORCING FILLERS

(75) Inventors: Huilin Tu, Watertown, MA (US); Agathe Robisson, Cambridge, MA (US)

(73) Assignee: SCHLUMBERGER TECHNOLOGY CORPORATION, Sugarland, TX (US)

( * ) Notice: Subject to any disclaimer, the term of this patent is extended or adjusted under 35 U.S.C. 154(b) by 76 days.

This patent is subject to a terminal disclaimer.

(21) Appl. No.: 13/335,086

(22) Filed: Dec. 22, 2011

(65) Prior Publication Data

US 2013/0164154 A1 Jun. 27, 2013

(51) Int. Cl.

| C08K 3/36 | (2006.01) |
|---|---|
| C08F 8/18 | (2006.01) |
| F04B 23/00 | (2006.01) |
| F04C 2/107 | (2006.01) |
| C07F 7/18 | (2006.01) |

(52) U.S. Cl.
CPC ............... C08K 3/36 (2013.01); C07F 7/1836 (2013.01); C08F 8/18 (2013.01); F04B 23/00 (2013.01); F04C 2/1075 (2013.01); F04C 2230/91 (2013.01); F05C 2225/04 (2013.01)

(58) Field of Classification Search
CPC ........... C08F 8/18; F04B 23/00; F04C 2/1075
USPC ...................................................... 525/326.3
See application file for complete search history.

(56) References Cited

U.S. PATENT DOCUMENTS

| 4,308,372 | A |   | 12/1981 | Smith, Jr. et al. |
|---|---|---|---|---|
| 4,387,203 | A | * | 6/1983 | Furuta et al. ................ 526/245 |
| 4,660,637 | A |   | 4/1987 | McGill et al. |
| 4,694,045 | A |   | 9/1987 | Moore |
| 4,860,581 | A |   | 8/1989 | Zimmerman et al. |
| 4,936,139 | A |   | 6/1990 | Zimmerman et al. |
| 5,026,786 | A |   | 6/1991 | Marchionni et al. |
| 5,214,115 | A | * | 5/1993 | Langstein et al. ............ 526/247 |
| 5,266,650 | A |   | 11/1993 | Guerra et al. |
| 5,311,952 | A |   | 5/1994 | Eddison et al. |
| 5,384,374 | A |   | 1/1995 | Guerra et al. |
| 5,617,926 | A |   | 4/1997 | Eddison et al. |
| 5,621,042 | A | * | 4/1997 | Hanada .................. C08F 8/42 525/102 |
| 5,674,959 | A |   | 10/1997 | Arcella et al. |
| 5,717,036 | A |   | 2/1998 | Saito et al. |
| 5,727,641 | A |   | 3/1998 | Eddison et al. |
| 6,090,491 | A | * | 7/2000 | Tan et al. .................... 428/421 |

(Continued)

FOREIGN PATENT DOCUMENTS

| CA | 2067891 A1 | 11/1992 |
|---|---|---|
| EP | 222201 B1 | 7/1990 |

(Continued)

OTHER PUBLICATIONS

Machine translation of JP 07-034059 A, Nov. 2015.*

(Continued)

*Primary Examiner* — Nichole M Buie-Hatcher
(74) *Attorney, Agent, or Firm* — Bridget M. Laffey

(57) ABSTRACT

Certain embodiments described herein are directed to silane functionalized fillers that may be, for example, covalently coupled to a polymer. In some examples, devices that include the filler reinforced polymer compositions are also described.

15 Claims, 6 Drawing Sheets

(56) References Cited

U.S. PATENT DOCUMENTS

| | | | |
|---|---|---|---|
| 6,186,227 B1 | 2/2001 | Vaynshteyn et al. | |
| 6,277,937 B1 * | 8/2001 | Duvalsaint et al. | 526/255 |
| 6,419,014 B1 | 7/2002 | Meek et al. | |
| 6,586,501 B1 | 7/2003 | Dalton et al. | |
| 7,289,285 B2 | 10/2007 | Barnes | |
| 7,331,581 B2 | 2/2008 | Xu et al. | |
| 7,363,970 B2 | 4/2008 | Corre et al. | |
| 7,392,851 B2 | 7/2008 | Brennan, III et al. | |
| 8,575,273 B2 * | 11/2013 | Tu et al. | 525/199 |
| 2003/0125463 A1 * | 7/2003 | Tatsu et al. | 525/101 |
| 2006/0147177 A1 * | 7/2006 | Jing et al. | 385/147 |
| 2007/0112149 A1 | 5/2007 | Hara et al. | |
| 2010/0092763 A1 * | 4/2010 | Kleiman-Shwarsctein et al. | 428/331 |
| 2010/0130687 A1 | 5/2010 | Tu et al. | |

FOREIGN PATENT DOCUMENTS

| | | |
|---|---|---|
| EP | 310966 B1 | 5/1993 |
| EP | 0784064 A1 | 7/1997 |
| JP | 3014838 | 1/1991 |
| JP | 3163148 | 7/1991 |
| JP | 05025422 Y2 | 2/1993 |
| JP | 5039294 | 2/1993 |
| JP | 6256567 | 9/1994 |
| JP | 07034059 A * | 2/1995 |
| JP | 11012330 A | 1/1999 |
| JP | 2003138127 | 5/2003 |
| JP | 2004131543 | 4/2004 |
| JP | 2007031708 A | 2/2007 |
| JP | 2007161999 | 6/2007 |
| RU | 2344139 | 1/2009 |

OTHER PUBLICATIONS

Caporiccio, G., Corti, C., Soldini, S. and Carniselli, G., "Perfluoropolyether Fluids for Vacuum Technologies," Industrial & Engineering Chemistry Product Research and Development, Sep. 1982, vol. 21(3): pp. 515-519.

Caporiccio, G., Corti, C., Soldini, S. and Rolando, A., "A New Perfluorinated Grease for High-vacuum Technology," Industrial & Engineering Chemistry Product Research and Development, Sep. 1982, vol. 21(3): pp. 520-522.

Matsumoto, A., Hirai, F., Sumiyama, Y., Aota, H., Takayama, Y., Kameyama, A. and Nakanishi, T., "Further Discussion of Steric Effect on the Radical Polymerization of Triallyl Isocyanurate as Compared with Its Isomer Triallyl Cyanurate: Polymerization and Copolymerization of Corresponding Trimethallyl Compounds," European Polymer Journal, 1999, vol. 35(2): pp. 195-199.

Matinlinna, J. P., Lassila, L. V. J., Yli-Urpo, A. and Vallittu, P. K., "An Introduction to Silanes and Their Clinical Applications in Dentistry," International Journal of Prosthodontics, 2004, vol. 17(2): pp. 155-164.

Matinlinna, J. P., Ozcan, M., Lassila, L. V. J. and Vallittu, P. K., "The Effect of a 3-methacryloxypropyltrimethoxy-silane and Vinyltrisopropoxysilane Blend and Tris (3-trimethoxysilylpropyl) Isocyanurate on the Shear Bond Strength of Composite Resin to Titanium Metal," Dental Materials, 2004, vol. 20(9): pp. 804-813.

Mealey, S. K. and Thomas, B., "Past, Present and Future of Organosilane Treatments for Filters," Rubber World, Dec. 2005: pp. 32-35, <http://www.dowcorning.com/content/publishedlit/26-1388-01.pdf>.

International Search Report and Written Opinion of PCT Application No. PCT/US2012/043206 dated Nov. 29, 2012: pp. 1-7.

Office Action for corresponding JP App No. 2014-548787, Dec. 7, 2015, 12 pages.

* cited by examiner $\phi > \phi*$ $\phi < \phi*$

ELASTOMER COMPOSITIONS WITH SILANE FUNCTIONALIZED SILICA AS REINFORCING FILLERS

TECHNOLOGICAL FIELD

Examples disclosed herein relate generally to silica-reinforced elastomer compositions. More particularly, certain embodiments disclosed herein are directed to silane coupling agents and/or silane-functionalized fillers effective to covalently couple a filler to a polymer such as, for example, a fluoropolymer.

BACKGROUND

Fillers can be added to elastomer compounds and other polymers. However, limited reinforcement effect of fillers is achieved due to the weak interactions between the fillers and the polymer.

SUMMARY

In one aspect, embodiments disclosed herein relate to a composition that includes a fluoropolymer covalently coupled to a filler through a silane coupling agent, the silane coupling agent having a chemically similar reactive moiety as a cure site moiety of the fluoropolymer to which the silane coupling agent is bonded.

In another aspect, embodiments disclosed herein relate to a method that includes reacting a filler with at least one silane coupling agent having the formula $Q_m$-Si—$Z_n$, where Z comprises one or more groups that can provide covalent attachment to the filler, Q is —R"-G or —CR'$_2$—CR'—R"-G, where R' is a hydrogen or a fluorine, R" is optional and is a linear or branched C1-C18 alkyl group, optionally containing one or more ether oxygen atoms and optionally fluorinated, G is a halogen, a nitrile group, or a vinyl group, and the sum of m+n is equal to four to covalently couple the silane to the filler; and reacting the covalently coupled silane-filler with a polymer to covalently couple the polymer to the covalently coupled silane-filler.

In yet another aspect, embodiments disclosed herein relate to a silane coupling agent having the formula of $Q_m$-Si—$Z_n$, where Z is one or more groups that can provide covalent attachment to a filler, Q is —R"-G or —CR'$_2$—CR'—R"-G, where R' is a hydrogen or a fluorine, R" is optional and is a linear or branched C1-C18 alkyl group, optionally containing one or more ether oxygen atoms and optionally fluorinated, G is a halogen, a nitrile group, or a vinyl group, and the sum of m+n is equal to four.

In yet another aspect, embodiments disclosed herein relate to a moving or progressive cavity motor or pump assembly having an inlet end and an outlet end, the motor or pump includes a housing and a rotor and a stator disposed within the housing. The surface of the rotor or the stator is made of an elastomer material which permits a seal to form between contacting surfaces of the rotor and the stator. The elastomer material comprises a polymer covalently coupled to a filler through a silane coupling agent, the silane coupling agent having a chemically similar reactive moiety as a cure site moiety of the fluoropolymer to which the silane coupling agent is bonded Additional aspects, examples, features and embodiments of the technology will be apparent to the person of ordinary skill in the art, given the benefit of the instant specification.

BRIEF DESCRIPTION OF THE FIGURES

Certain features, aspect and examples are described in more detail below with reference to the accompanying figures in which.

Figure 1A:
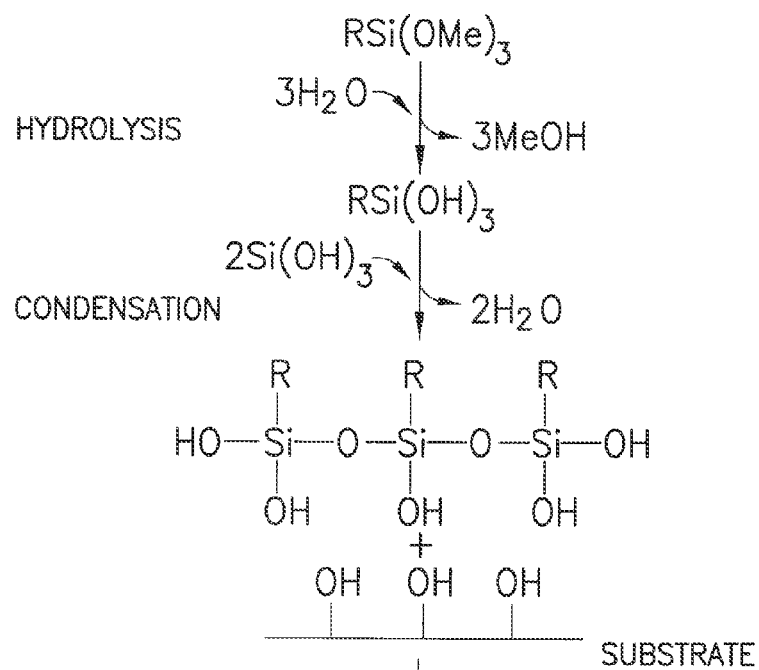
FIGS. 1A-1C show one process of covalently coupling a silane coupling agent to a surface of a filler, in accordance with certain examples.

It will be recognized by the person of ordinary skill in the art, given the benefit of this disclosure, that the compounds shown in the figures and used throughout the text may be shown with disproportionate bond lengths, bond angles and the like to facilitate a better understanding of the technology described herein. Unless otherwise specified, no particular stereochemistry is implied in the illustrative chemical compounds drawn and described herein.

DETAILED DESCRIPTION

Certain examples described herein provide advantages over existing coupling agents and/or fillers and materials produced using such coupling agents and/or fillers including, but not limited to, improved elastic modulus stability at high temperature, reduction of the Payne effect in fillers modified with the silane coupling agents (i.e., reduced tangent delta), and increased use life of parts or components produced using the materials disclosed herein. These and other advantages will be recognized by the person of ordinary skill in the art, given the benefit of this disclosure.

Certain embodiments of the polymers produced using the coupling agents and/or fillers disclosed herein may be used in numerous industrial, medical and mechanical applications, and are particularly suited for environments where high temperature, high pressure, aggressive chemicals and mechanical loads may be required or encountered. For example, certain embodiments of the cross-linked polymers may be particularly suited for use in oil field service (OFS) industry such as, for example, the heavy oil market in: (1) structural component and insulation applications such as electrical pads and cables, feed-through, housing and packaging material of electrical and chemical devices, valves, pumps, and etc.; (2) elastomeric applications: general-purpose seals including o-rings and gaskets, packers for exploration and production tools including mechanical packers, inflatable packers and swellable packers, mud motor, actuators, cables and etc. Certain examples of polymers produced using the coupling agents and/or fillers and other materials disclosed herein may also be used in down-hole applications such as chemical, wear, and heat resistant piping, sleeves, wire and cable jacketing, coatings, connectors, liners, tubes and similar devices. In addition, the polymers disclosed herein have additional uses such as, for example, in snap fit parts, parts used in load bearing applications, heat shrinkable molded parts, and other parts used in the electrical, automotive, aerospace, medical industries and oil field service industries.

In certain embodiments, the polymers produced using the coupling agents and/or fillers disclosed herein may be used by themselves or in combination with one or more other polymers, metals or non-metals, or structural components to provide an assembly configured for a desired use. These and other applications and uses of the materials described herein will be readily selected by the person of ordinary skill in the art, given the benefit of this disclosure.

The compositions produced using the silane functionalized fillers described herein provide for covalent coupling of the polymer to the filler through the silane functionalization. The term covalent coupling refers to attachment through one or more covalent bonds but not necessarily direct attachment to a particular species without any intervening atoms. The fillers may be pre-modified with the silane functionalization prior to being compounded with the polymer or may be reacted with the silane during compounding.

Fillers used in fluoroelastomer compounds are different from those in conventional elastomers. Limited reinforcement effects of active fillers are observed due to the weak interactions at the interface of active fillers and fluoroelastomers. Non-active or low active carbon black or mineral fillers in loadings up to 50 phr may be used. In non-limiting examples, MT-black N990 filler is used because of its large particle size and low structure, as well as its lower pH that leads to shorter curing time. Other fillers including various grades of other carbon blacks, fibrous calcium silicate, barium sulfate, titanium oxide, iron oxide, silica, poly(tetrafluoroethylene) (PTFE) powders, etc., may also be used.

Strong interactions can be achieved at the filler-fluoropolymer interface if the fillers are covalently bound to the polymers. Silane coupling agents, which are capable of forming covalent bonds directly to the polymer, can be used to enhance the adhesion between the polymer and the fillers, such as silica fillers. The fillers may be pre-modified with the silane coupling agents to possess silane functionalization prior to being compounded with the polymer or the fillers may be reacted with the silane coupling agent during compounding. In either case, the silane may covalently bind the filler to the polymer and thus be referred to a silane coupling agent. In embodiments, the silane coupling agent may possess at least one moiety that is the same as the reactive or cure site monomer or moiety of the polymer being modified.

Certain embodiments described herein are directed to thermally stable silane coupling agents which are effective to provide covalent bonding between silica fillers and fluoroelastomers, perfluoroelastomers, fluoroplastics and other polymers. The advantages provided in at least certain embodiments include, but are not limited to: (1) the reactivity of the cure site moiety in these silane coupling agents should be the same as or chemically similar to the cure site moiety on the polymer so that the silane coupling agent can react well with the polymer matrix to form cross-links providing a reinforcing effect; (2) the thermal stability of these silanes and the produced cross-links are excellent so that reinforcing effect will be present even at high temperatures; and/or (3) similar to conventional coupling agents, these functional silanes can also improve the dispersion of silica fillers by changing their surface polarity.

In one embodiment, the silane coupling agents have a general structure as shown in formula (I):

(I)

where Q comprises one or more groups that can provide covalent attachment to the polymer and Z comprises one or more groups that can provide covalent attachment to the filler.

In certain embodiments, the Z group of formula (I) may be selected such that reaction with one or more groups on the filler surface results in covalent bond formation between the coupling agent and the filler. In certain examples, Z may be a hydrolyzable group including, but not limited to, a hydroxy, an alkoxy, an acyl-oxyl, a halogen, an amine or other suitable hydrolyzable group. In some examples, the Z group(s) may be labile and cleaved or otherwise removed through dehydration or other suitable mechanisms such that the Si group of formula (I) can covalently bond to a surface moiety on the filler to covalently couple the silane to the filler. For example, Z may be a hydroxyl group that can protonate and leave as water with subsequent or concurrent formation of a covalent bond between the filler and the coupling agent. In some examples, Z may be an alkyl group comprising a hydroxyl group including, but not limited to, methoxy, ethoxy, propoxy, butanoxy or other oxygen containing alkyl groups which may be saturated or unsaturated. In addition, where more than one Z group is present, the Z group may be the same or may be different.

The sum of m+n is normally equal to four, with each of m and n independently selected from zero, 1, 2, 3 and 4. In some examples, n is 3 and m is 1 or n is 2 and m is 2 or n is 1 and m is 3. It is also possible for m to be 4 and n to be zero or for m to be zero and n to be 4 depending on the exact substituents selected for Q and Z.

As mentioned above, in embodiments, the silane coupling agent may possess at least one moiety that is the same as or chemically similar to the reactive or cure site moiety of the polymer being modified. This cure site moiety on the silane coupling agent may be represented as Q in formula (I) above. The cure site moiety of the polymer being modified may depend on the particular curing mechanism being used. For example, a free radical curing mechanism may require a cure site monomer, discussed below, to be incorporated into the polymer backbone to allow for crosslinking. By having a similar moiety as the cure site monomer present in a silane coupling agent, the polymer may also form covalent bonds with the filler (through the silane coupling agent) during curing of the polymer. Cure site monomers may generally have the formula $CR'_2=CR'-R''-G$, where R' is a hydrogen or a fluorine, R'' is optional and may be a linear or branched alkylene group, optionally containing one or more ether oxygen atoms and optionally fluorinated, and G is a halogen, such as Br or I, a nitrile group, or a vinyl group. Thus, Q may have a similar chemistry of $-CR'_2-CR'-R''-G$ or $-R''-G$, where R' is a hydrogen or a fluorine, R'' is a linear or branched C1-C18 alkyl group, optionally containing one or more ether oxygen atoms and optionally fluorinated, and G is a halogen, such as Br or I, a nitrile group, or a vinyl group.

For fluoropolymers not containing a cure site monomer, such as polymers cured by a bisphenol or diamine curative, curing may involve dehydrofluorination at a vinylidene fluoride site, followed by nucleophilic substitution by a hydroxy group of bisphenol or an amine addition. Thus, in such cases, the silane coupling agent may include a terminal vinylidene fluoride group, i.e., Q may have a chemistry of $-CR'_2-CR'-R''-CR'=CR'_2$ or $-R''-CR'=CR'_2$, where R' is a hydrogen or a fluorine, R'' is optional and may be a linear or branched C1-C18 alkyl group, optionally containing one or more ether oxygen atoms and optionally fluorinated.

In certain embodiments, the silane coupling agent may take the form of a compound as shown in the below formulae:

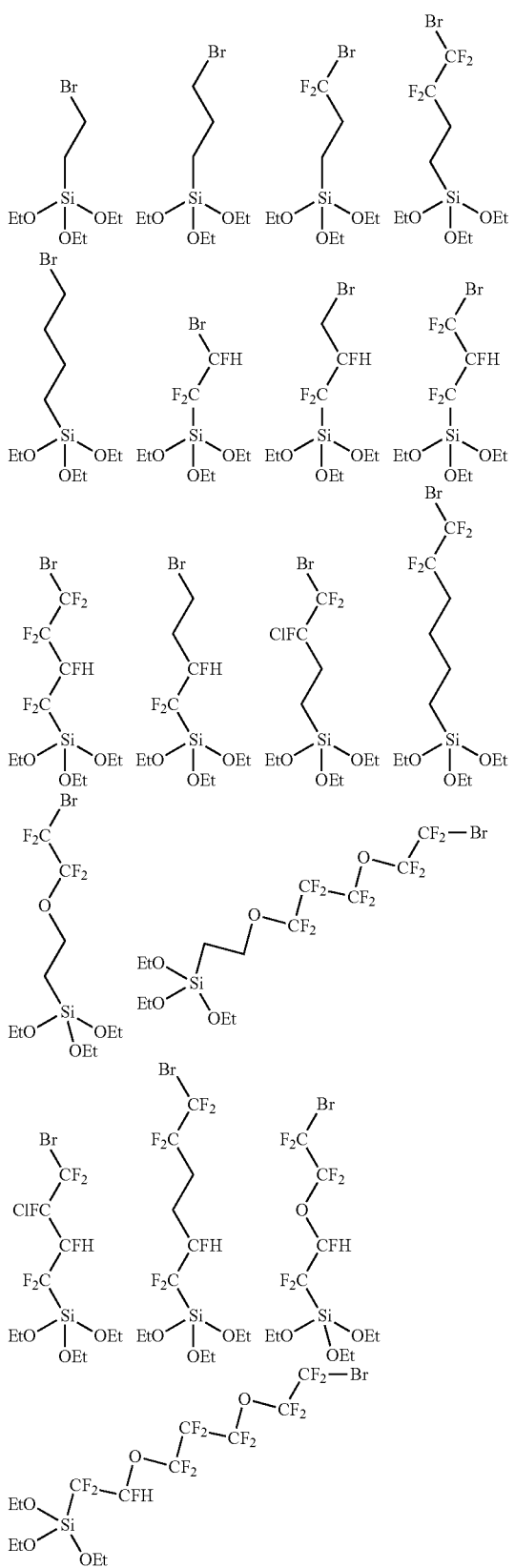

In the above formulae, the Q group is shown to be based on reaction of a silane with CR'$_2$=CR'—R"-G containing a vinyl (or vinylidene fluoride) group. It is envisioned that the Q group on the silane may be the same as the pendant group of the cure site monomer hanging off of the polymer backbone, or the cure site monomer may be reacted with a silane (as shown above) through a vinyl or vinylidene fluoride group such that there additional C2 group within Q as compared to the pendant group of the cure site monomer extending from the polymer backbone and thus the Q group is the same as the cure site monomer chemistry (pre-polymerized). Further, while ethoxy groups are shown as the Z substituents in the above formulae, it is intended that any Z group described above, including hydroxyl, alkoxy, acyl-oxyl, halogen and amine groups may be used, in any combination within a single coupling agent.

The silane coupling agent may be present in amounts ranging from 0.5 to 25 parts per hundred parts of resin. In another embodiment, the silane coupling agent may be present in an amount ranging from 0.1 to 5 parts per hundred parts of resin.

The illustrative examples of the silane coupling agents described herein may be synthesized using known methods of producing silane compounds. For example, halo- or alkoxysilanes may be reacted with Grignard reagents (RMgX where R is an organic group and X is a halogen) or alkali metal organics, e.g., RLi where R is an organic group as shown in the reaction schemes below.

$$RMgCl + HSiCl_3 \rightarrow RHSiCl_2 + MgCl_2$$

$$RLi + SiCl_4 \rightarrow RSiCl_3 + LiCl$$

Another method of synthesizing silane coupling agents is through hydrosilyation of an olefin in the presence of a catalyst such as, for example, chrloroplastinic acid, t-butylperoxide and amine complexes. The silicon in general ends up on the least substituted carbon.

$$RCH=CH_2 + HSiCl_3 \rightarrow RCH_2CH_2SiCl_3$$

Hydrosilylation may occur, for example, in the presence of Karstedt catalyst (Pt$_2${[(CH2=CH)Me$_2$Si]$_2$O}$_3$) to silylate an unsaturated side chain. In other examples, organosilanes may also be produced by direct synthesis of an organohalide with silicon using heat and a copper catalyst.

$$RCl + Si \rightarrow RSiCl_3 + R_2SiCl_2 + R_3SiCl$$

Figure 1B:
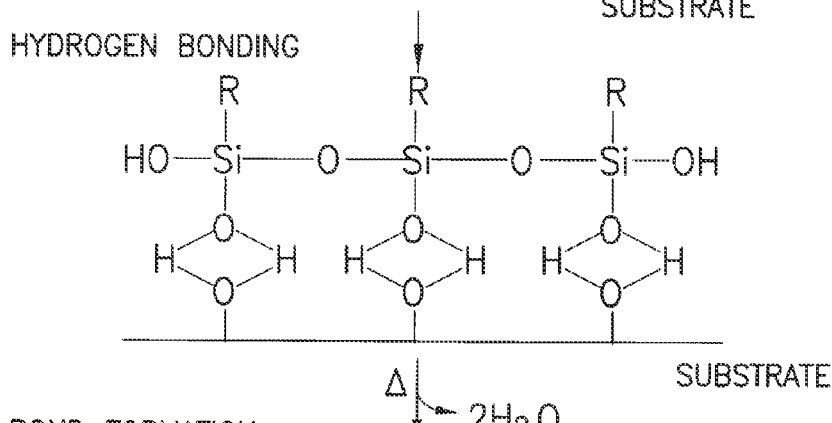
Figure 1C:
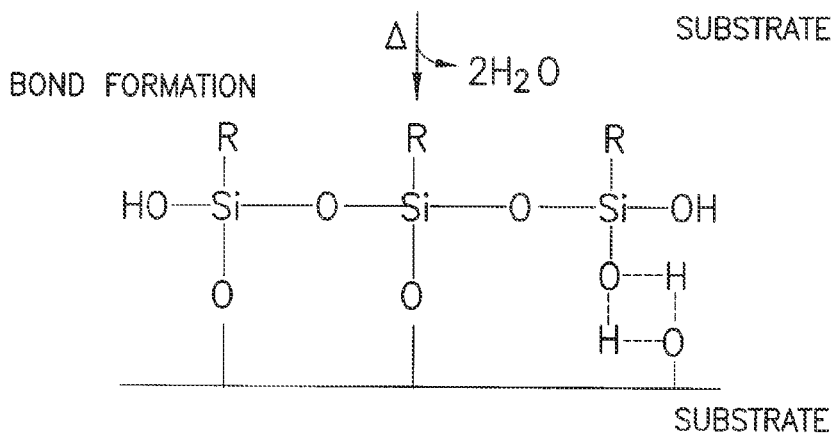

In certain embodiments, the silane coupling agents may react with the filler through various mechanisms. In one route, the silane may first react with additional silane coupling agents to provide a condensed product having polysiloxy linkages. Next, hydrogen bonding of the organo group(s) of the silane to the surface of the filler may first occur. Protons from the surface may be donated to the organo groups of the coupling agent followed by loss of water (dehydration) and subsequent linkage between the filler surface and the silane may then occur with loss of water. An illustration of the overall process is shown in FIGS. 1A-C using a generic silane.

Illustrative organo groups that may be used in the silane coupling agents include, but are not limited to, —SiCl$_3$, —SiBr$_3$, —SiF$_3$, —Si(OMe)$_3$, —Si(OEt)$_3$, —Si(OnPr)$_3$, —Si(OnBu)$_3$, —Si(OEtBu)$_3$, and —Si(OAc)$_3$ where Me is methyl, Et is ethyl, nPr is n-propyl, nBu is n-butyl, and Ac is acetyl. The substituents of the silane group need not be the same. In some examples, three of the substituents may be the same, two of the substituents may be the same or the three substituents may be different. It is desirable that the substituents of the silane be hydrolyzable groups whether or not the substituents are the same or not.

In certain embodiments, to synthesize the silane coupling agent compounds, the base structure may be hydrosilylated, e.g., a Q-Cl base structure can be hydrosilylated. For example, hydrosilylation of Q-Cl with proper tri-functional (triethoxy, trimethoxy, or trichloro) silanes at the presence of Karstedt catalyst can provide the silane coupling agents.

In certain embodiments, by modifying the filler surface, different properties are achieved. First, the surface polarity of the silica filler is dramatically changed. For example, before silanization, silica fillers (fumed or precipitated) have very high surface energy. They tend to form large agglomerates in a polymer matrix which often become the crack-initiation sites and thus degrade the mechanical properties of the composites. When silica fillers are treated with silane coupling agents, their surface energy is lowered and it becomes similar to that of fluoroelastomers. These modified fillers will absorb much less moisture, or even not absorb water vapor if complete silane coverage is achieved. As a result, the fillers will disperse well in fluoroelastomers when compounded with fluoroelastomer gums. Second, the silanes are reactive. At the curing conditions of fluoroelastomers and etc., the cure site moiety of these silanes will react (leading to cross-links at the filler surfaces) with the cure site moieties on the polymers and thus bind the fillers covalently to the polymers. For example, there may be covalently bound rubber on the filler surfaces. The bound rubber can affect the mechanical properties of rubbers.

When comparing bound rubber content and properties in different systems or at different conditions for one particular polymer-filler system, several factors should be considered as bound rubber is sensitive to the chemical and physical nature of the polymers and fillers, as well as the experimental conditions (temperature, solvent and etc.) at which the bound rubber is isolated and measured. Covalent bound rubber obtained using the silane coupling agents described herein is very different from that in polyolefin-carbon black systems where physical attractions tether the polymer layer near the filler surfaces. The bond dissociation energies of silicon-oxygen, silicon-carbon and carbon-carbon (single) bonds, which are the major types of chemical bonds at the cure site moiety-silane series modified silica surface, are about 370-570 kJ/mol. As a comparison, the absorption energy of polyolefins on carbon blacks is in general about 10-35 kJ/mol (at least one order of magnitude weaker). The exceptionally strong bonding present in the covalently bound rubber can assist in providing excellent high-temperature resistance of the polymer compounds.

Figure 2:
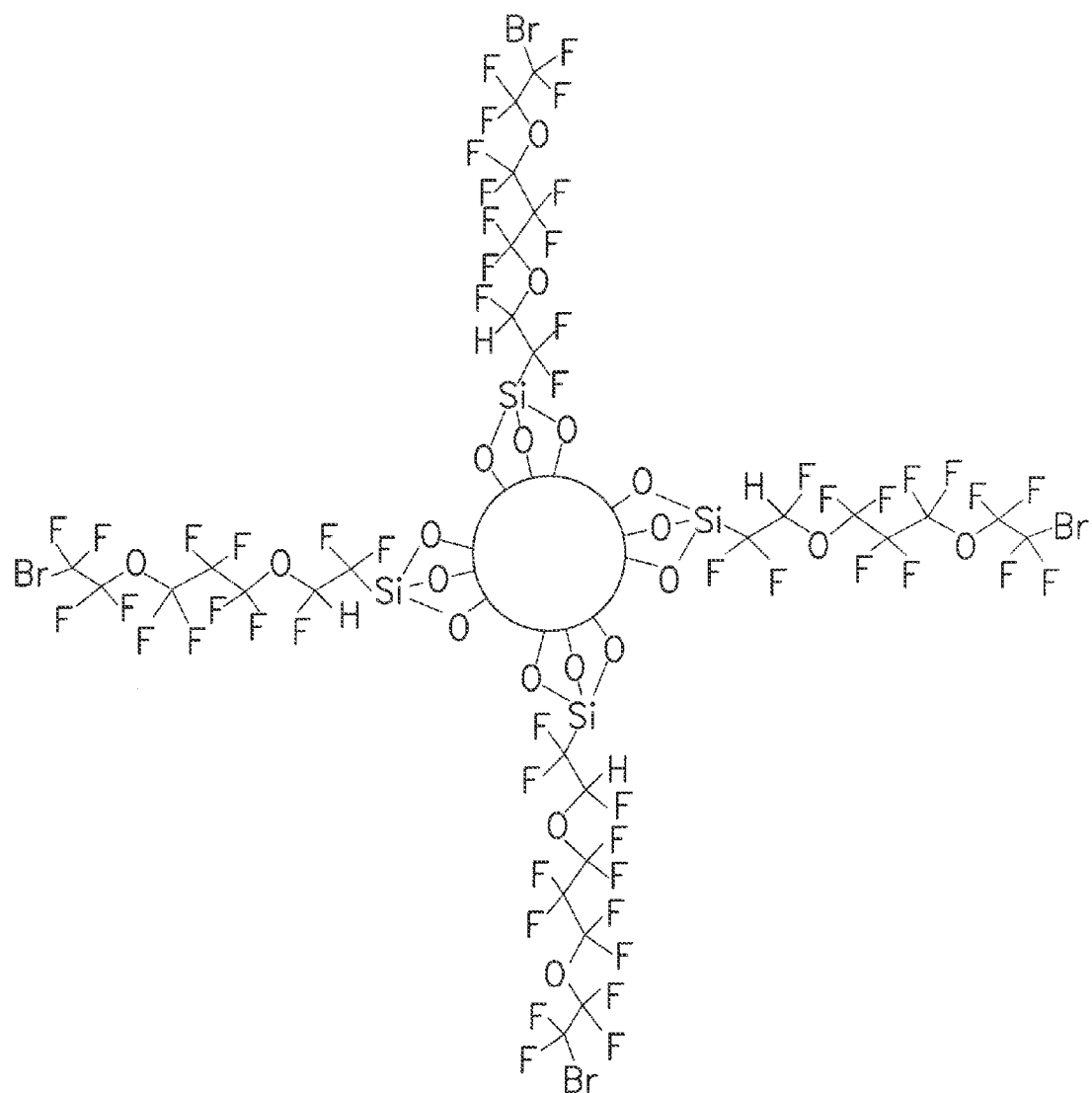
FIG. 2 is an illustration of a filler particle covalently coupled to a silane coupling agent, in accordance with certain examples.

In certain embodiments, the surface modification of silicate surfaces using these silane coupling agents can be carried out by standard procedures. The coupling agents can be applied to the substrates by deposition from aqueous alcohol, deposition from aqueous solution, bulk deposition onto powders by a spray-on method, integral blend method, anhydrous liquid phase deposition, vapor phase deposition, spin-on deposition and spray application. For chlorosilanes, they can be deposited from alcohol solution. Notwithstanding which particular application procedure may be selected, the reaction of the silane coupling agents can be categorized into four steps for convenience purposes. First, hydrolysis of the three hydrolyzable groups occurs (water is present in the solvent or absorbed at the surface from air). Condensation to oligomers follows. The oligomers then form hydrogen bonds with hydroxyl group on the surface. Finally, during drying or curing, a covalent linkage is formed with the substrate with concomitant loss of water. One example of the hydrolytic deposition of silanes is shown in FIGS. 1A-C. An illustration showing a cure site moiety-containing silane covalently coupled to the surface of a silica particle is shown in FIG. 2. In use, the silica filler is seldom present as a single spherical particle as shown in FIG. 2. In many instances, the silica fillers arrange themselves similar to strings of pearls.

In certain embodiments, an excess of silane coupling agent may be used such that substantially all accessible hydroxyl sites (or other reactive sites) on the filler surface can be modified with a silane coupling agent. In other examples, complete coverage with silane coupling agents may not be required. High-temperature silanes such as phenyltriethoxysilane, pentafluorophenyltriethoxysilane, p-tolyltrimethoxysilane, p-trifluoromethyltetrafluorophenyl-triethoxysilane and etc. can be mixed with the silane coupling agents to dilute the surface concentration of the coupling silanes. These high-temperature silanes serve as covering agents which modify the surface polarity of the fillers and do not form covalent bonds to any substantial degree.

In certain examples, the exact filler used with the silane coupling agents is not of great consequence. In particular many different types of fillers may be used, and in certain instances more than one type of filler may be used. Illustrative types of fillers that can be used include, but are not limited to, silica, precipitated silica, amorphous silica, vitreous silica, fumed silica, fused silica, quartz, glass, aluminum, aluminum-silicate (e.g., clays), copper, tin, talc, inorganic oxides (e.g., $Al_2O_3$, $Fe_2O_3$, $TiO_2$, $Cr_2O_3$), steel, iron, asbestos, nickel, zinc, silver, lead, marble, chalk, gypsum, barites, graphite, carbon black, treated carbon black such as, for example, silicon treated carbon black and other particles, powders and materials that include, or can be chemically modified to include, one or more surface reactive groups. Fumed silica Cab-o-Sil M5 (Cabot) is one example of a filler than can be used. Fillers may be incorporated in amounts ranging from about 1 to 50 parts per hundred parts of resin. Some embodiments may use at least 2 parts per hundred parts of resin, at least 5 parts per hundred parts of resin, at least 10 parts per hundred parts of resin or at least 20 parts per hundred parts of resin.

Similar to the fillers, the exact polymer used with the silane coupling agents may vary. In one embodiment, polymers that include one or more of a double bond, halogen, leaving groups or that can react by free radical, amine curing, bisphenol curing, or thermal curing mechanisms may be used with the silane coupling agents described herein. Illustrative polymers include, but are not limited to a high density polyethylene, a nylon, a polycarbonate, a polyether sulfone, a polyphenylene oxide, a polyphenylene sulfide, a polypropylene, a polystyrene, a polyurethane, a polysulfone, a polyvinylchloride, a polyamide, a polyimide, a polyamide-imide, a polybutylene, a polybutylene terphthalate, a polyepoxide and other polymers. In some examples, a single type of polymer, different polymers, blends of polymers and the like may be used. Thus, in examples described herein that use a fluoropolymer in combination with a coupling agent, the fluoropolymer may be substituted with, or used in combination with, one or more other polymers. In some examples, the coupling agent may be particularly suited for use with polymers in high temperature applications such as, for example, those greater than or equal to about 150° C.

In one embodiment, a halopolymer such as a fluoropolymer, a chloropolymer, and a bromopolymer may be used. Mixed halo polymers including two or more different halo substituents, such as, for example, chlorofluoropolymers and bromofluoropolymers, may also be used. Halopolymers may also include heteroatoms including, but not limited to, nitrogen, oxygen, sulfur and heterogroups formed from nitrogen, oxygen and sulfur. Of particular interest for use with the cross-linkers disclosed herein are fluoropolymers, which are difficult to cross-link due to the inertness of the carbon-fluorine bond. Fluoroelastomers in general are synthesized by radical co-, ternary or tetrapolymerizations of fluoroalkenes. Examples of fluoroelastomers include copolymers comprising units of vinylidene fluoride (VDF or $VF_2$) and units of at least one other copolymerizable fluorine-containing major monomer such as tetrafluoroethylene (TFE), hexafluoropropylene (HFP), chlorotrifluoroethylene (CTFE), vinyl fluoride (VF), ethylene (E), propylene (P), and a perfluoro(alkyl vinyl ether) (PAVE). Specific examples of PAVE include perfluoro (methyl vinyl ether) (PMVE), perfluoro(ethyl vinyl ether) and perfluoro(propyl vinyl ether). Depending on the type of curing mechanism to be used, the polymer may also incorporate at least one cure site monomer therein to allow a radical to be formed by a peroxide and then crosslinked by a co-agent. Cure site monomers may be incorporated into fluoroelastomer in an amount ranging from about 0.1 to about 10 (or from about 0.2 to about 5) weight percent, based on the total composition of the fluoroelastomer. The remaining units in the fluoroelastomers may be comprised of at least two different copolymerized monomers, different from each other and said cure site monomer, selected from the group consisting of fluoromonomers, hydrocarbon olefins and mixtures thereof. Fluoromonomers include both fluorine-containing olefins (fluoroolefins) and fluorine-containing vinyl ethers (fluorovinyl ethers). Specific examples of fluoroelastomers that may be employed (cure site monomers omitted for clarity) include, but are not limited to copolymerized units of TFE/PMVE, $VF_2$/PMVE, $VF_2$/TFE/PMVE, TFE/PMVE/E, TFE/P and TFE/P/$VF_2$.

Examples of suitable cure site monomers include, but are not limited to: i) bromine-containing olefins; ii) bromine-containing vinyl ethers; iii) iodine-containing olefins; iv) iodine-containing vinyl ethers; v) fluorine-containing olefins having a nitrile group; vi) fluorine-containing vinyl ethers having a nitrile group; and vii) non-conjugated dienes.

Brominated cure site monomers may contain other halogens, such as fluorine. Examples of brominated olefin cure site monomers are bromotrifluoroethylene (BTFE); 4-bromo-3,3,4,4-tetrafluorobutene-1 (BTFB); vinyl bromide; 1-bromo-2,2-difluoroethylene; perfluoroallyl bromide; 4-bromo-1,1,2-trifluorobutene-1; 4-bromo-1,1,3,3,4,4-hexafluorobutene; 4-bromo-3-chloro-1,1,3,4,4-pentafluorobutene; 6-bromo-5,5,6,6-tetrafluorohexene; 4-bromoperfluorobutene-1 and 3,3-difluoroallyl bromide. Brominated vinyl ether cure site monomers may include 2-bromo-perfluoroethyl perfluorovinyl ether and fluorinated compounds of the class $CF_2Br$—$R_f$—O—CF=$CF_2$ ($R_f$ is a perfluoroalkylene group), such as $CF_2BrCF_2O$—CF=$CF_2CF_2$=CFOCF$_2$CF$_2$CF$_2$OCF$_2$CF$_2$Br, and fluorovinyl ethers of the class ROCF=CFBr or ROCBr=$CF_2$ (where R is a lower alkyl group or fluoroalkyl group) such as $CH_3$OCF=CFBr or $CF_3CH_2$OCF=CFBr.

Suitable iodinated cure site monomers include iodinated olefins of the formula: CHR=CH-L-$CH_2$CHR—I, wherein R is —H or —$CH_3$; L is a $C_1$-$C_{18}$ (per)fluoroalkylene radical, linear or branched, optionally containing one or more ether oxygen atoms, or a (per)fluoropolyoxyalkylene radical as disclosed in U.S. Pat. No. 5,674,959. Other examples of useful iodinated cure site monomers are unsaturated ethers of the formula: I($CH_2CF_2CF_2$)$_n$OCF=$CF_2$ and ICH$_2$CF$_2$O[CF (CF$_3$)CF$_2$O]$_n$CF=$CF_2$, and the like, wherein n=1-3, such as disclosed in U.S. Pat. No. 5,717,036. In addition, suitable iodinated cure site monomers including iodoethylene, 4-iodo-3,3,4,4-tetrafluorobutene-1 (ITFB); 3-chloro-4-iodo-3,4,4-trifluorobutene; 2-iodo-1,1,2,2-tetrafluoro-1-(vinyloxy)ethane; 2-iodo-1-(perfluorovinyloxy)-1,1,-2,2-tetrafluoroethylene; 1,1,2,3,3,3-hexafluoro-2-iodo-1-(perfluorovinyloxy)propane; 2-iodoethyl vinyl ether; 3,3,4,5,5,5-hexafluoro-4-iodopentene; and iodotrifluoroethylene are disclosed in U.S. Pat. No. 4,694,045. Allyl iodide and 2-iodoperfluoroethyl perfluorovinyl ether may also be useful cure site monomers.

Useful nitrile-containing cure site monomers may include those of the formulas shown below. $CF_2$=CF—O($CF_2$)$_n$—CN where n=2-12; $CF_2$=CF—O[$CF_2$—CF($CF_3$)—O]$_n$—$CF_2$—CF($CF_3$)—CN where n=0-4; $CF_2$=CF—[OCF$_2$CF (CF$_3$)]$_x$—O—(CF$_2$)$_n$—CN where x=1-2, and n=1-4; and $CF_2$=CF—O—(CF$_2$)$_n$—O—CF($CF_3$)CN where n=2-4.

Examples of non-conjugated diene cure site monomers include, but are not limited to 1,4-pentadiene; 1,5-hexadiene; 1,7-octadiene; 3,3,4,4-tetrafluoro-1,5-hexadiene; and others, such as those disclosed in Canadian Patent 2,067,891 and European Patent 0784064A1. A suitable triene is 8-methyl-4-ethylidene-1,7-octadiene.

Of the cure site monomers listed above, for situations wherein the fluoroelastomer will be cured with peroxide, brominated or iodinated cure such monomers such as 4-bromo-3,3,4,4-tetrafluorobutene-1 (BTFB); 4-iodo-3,3,4,4-tetrafluorobutene-1 (ITFB); allyl iodide; bromotrifluoroethylene, or a nitrile-containing cure site monomer such as perfluoro(8-cyano-5-methyl-3,6-dioxa-1-octene) may be used. When the fluoroelastomer will be cured with a polyol, 2-HPFP or perfluoro(2-phenoxypropyl vinyl) ether may be used. When the fluoroelastomer will be cured with a tetraamine, bis(aminophenol) or bis(thioaminophenol), a nitrile-containing cure site monomer (e.g., 8-CNVE) may be used. When the fluoroelastomer will be cured with ammonia or a compound that releases ammonia at curing temperatures (e.g., urea), a nitrile-containing cure site monomer (e.g., 8-CNVE) may be used. Further, it is also within the scope of the present disclosure that other cure site monomers may be used, where the silane coupling agent would possess the same type of chemical moiety for its Q group as the selected cure site monomer.

Some embodiments may involve a silane coupling agent having a chemically identical Q group as the cure site moiety on the polymer. Some embodiments may involve a silane coupling agent having a chemically identical Q group as the pendant group of the cure site monomer. Other embodiments may involve a silane coupling agent having a chemically similar Q group as the pendant group of the cure site monomer, i.e., if the cure site monomer is a bromine-containing olefin, such as those described above, the Q group may be any bromine-containing alkyl group.

In certain embodiments, fluoroelastomers can also be produced in an emulsion polymerization process using a water-soluble polymerization initiator and an excess amount of surfactant. The resulting fluoroelastomer may exit the reactor in the form of a latex which is degassed (e.g., freed from unreacted monomers), coagulated, filtered and washed. Fluoroelastomers can also be produced in a suspension polymerization process, where polymerization is carried out by dispersing one or more monomers, or an organic solvent with monomer dissolved therein, in water and using an oil-soluble organic peroxide. No surfactant or buffer in general is used and fluoroelastomer is produced in the form of polymer particles which may be directly filtered, e.g., without the need for coagulation, and then washed, thus producing a cleaner polymer than that resulting from an emulsion process. Also, the fluoroelastomer polymer chains are substantially free of ionic end groups so that the Mooney viscosity is relatively low and the polymer has improved processability compared to polymer produced by an emulsion process.

In certain embodiments, perfluoroelastomers can be used with the silane modified fillers described herein. Perfluoroelastomers are generally amorphous polymeric compositions having copolymerized units of at least two principal perfluorinated monomers. Generally, one of the principal monomers is a perfluoroolefin while the other is a perfluorovinyl ether. Representative perfluorinated olefins include tetrafluoroethylene and hexafluoropropylene. Suitable perfluorinated vinyl ethers include those of the formula $CF_2=CFO(R_mO)_n(R_kO)_jR_f$ where $R_m$ and $R_k$ are different linear or branched perfluoroalkylene groups of 2-6 carbon atoms, m, n and j are independently 0-10, and $R_f$ is a perfluoroalkyl group having 1-6 carbon atoms. Perfluoroelastomers have achieved outstanding commercial success and are used in a wide variety of applications in which severe environments are encountered, in particular those end uses where exposure to high temperatures and aggressive chemicals occurs. For example, these polymers are often used in seals for aircraft engines, in oil-well drilling devices, and in sealing elements for industrial equipment used at high temperatures. The outstanding properties of perfluoroelastomers can be attributed to the stability and inertness of the copolymerized perfluorinated monomer units that make up the major portion of the polymer backbones in these compositions. Such monomers include tetrafluoroethylene and perfluorinated vinyl ethers. In order to develop elastomeric properties fully, perfluoroelastomers are in general cross-linked, e.g., vulcanized. To this end, a small amount of cure site monomer can be copolymerized with the perfluorinated monomer units.

In other embodiments, poly(perfluoro-alkylene oxides) terminated with polymerizable functional groups can be polymerized to prepare certain polymers, e.g., polyurethanes, having low glass transition temperatures and low-temperature flexibility. For example, poly(perfluoroalkylene oxide) peroxides can be used with ethylenically unsaturated monomers in making block copolymers having good low-temperature flexibility. Fluorinated ethers with nonfunctional terminal moieties are sold under the trademarks "Krytox" and "Fomblin" for use as vacuum pump fluids, see e.g., G. Caporiccio et al., 21 IND. ENG. CHEM. PROD. RES. DEV. 515-19 (1982).

In certain examples, compositions of fluoroelastomers cross-linked with dihydroxypolyfluoroethers may be used. The dihydroxypolyfluoroethers may contain either branched moieties, are random copolymers containing —$CF_2O$— repeating units or contain partially fluorinated repeat units. In other examples, perfluoropolyether polymers may be prepared as described, for example, in U.S. Pat. No. 5,026,786. These perfluoropolyethers comprise randomly distributed perfluoroxyalkylene units. European Pat. Pub. No. 222,201 describes vulcanizable rubber blends comprising certain perfluoropolyether which can also be used with the coupling agents described herein. These perfluoropolyethers have brominated or fluorinated end groups. European Pat. Pub. No. 310,966 describes rubber blends comprising certain perfluoropolyethers. These perfluoropolyethers comprise perfluoroalkyl end groups.

In certain embodiments, certain classes of fluorinated ether compositions comprising functional fluoroaliphatic mono- and polyethers may be used, as described, for example, in U.S. Pat. Nos. 5,384,374 and 5,266,650.

The polymers suitable for use with the silane modified fillers including, but not limited to, fluoroelastomers, perfluoroelastomers and the like, are commercially available from numerous sources including, but not limited to, DuPont Performance Elastomers LLC (Wilmington, Del.), DuPont-Mitsui Fluorochemicals Co. (Japan), AGC Chemicals America (Exton, Pa.), Solvay Solexis (Italy), Daikin Industries (Japan), Zeon Corporation (Japan), Exfluor Research Corporation (Austin, Tex.) and other chemical suppliers.

Figure 3:
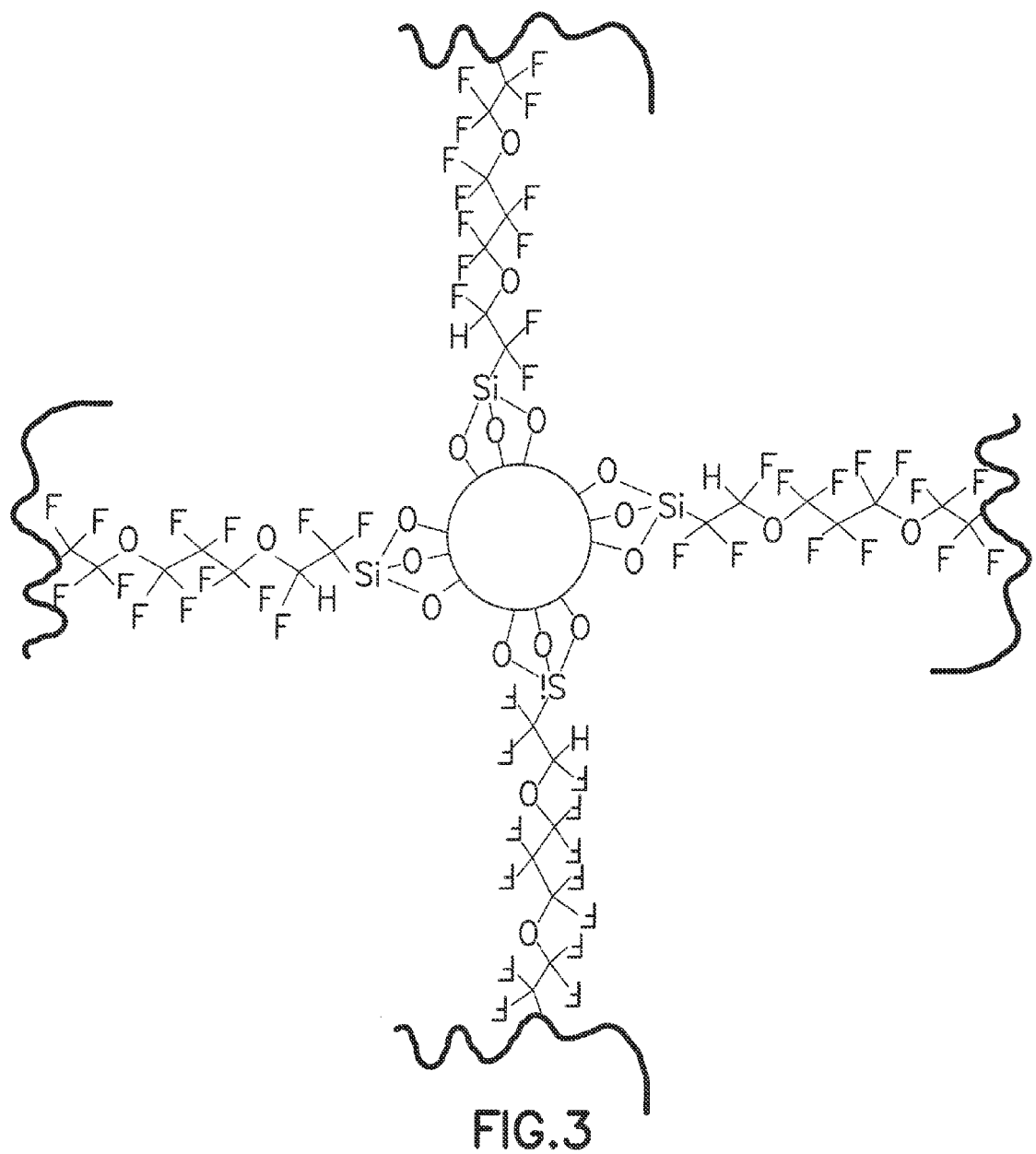
FIG. 3 is an illustration of a filler particle covalently coupled to a polymer through a silane coupling agent, in accordance with certain examples.

In preparing the compositions, the silane coupling agent may be linked to the filler surface in a first step and the resulting product can be reacted with the polymer in a second step. In other examples, the silane coupling agent may be reacted with the polymer in a first step and then reacted with the filler surface in a second step. In yet other examples, the polymer, filler and silane coupling agent may be mixed or blended together to provide a composition that includes a polymer coupled to a filler through the silane coupling agent. Notwithstanding the exact sequence of event used, the resulting composition includes a filler covalently coupled to a polymer through the silane coupling agent. An illustration of the resulting composition is shown in FIG. 3.

In certain examples, free radicals are first generated using suitable species such as, for example, branched alkyl molecules including one or more heteroatoms such as, oxygen, nitrogen or sulfur. In this initiation step, the free radicals may be generated by exposing the alkyl molecules to light, heat, initiators such as peroxides (organic peroxides which are particularly effective curing agents for fluoroelastomers include dialkyl peroxides which decompose at a temperature above 50° C.), chlorine gas, bromine or other commonly employed free radical initiators. The formed free radicals may react with the silane-modified fillers to form silane-modified fillers that include a free radical. The free radical filler can react with the polymer in one or a series of propagation steps to covalently couple the polymer to the silane modified filler and/or to generate more free radicals. In one or more termination steps, the free radical filler may react with multiple polymer molecules and result in polymer being covalently coupled to the filler through the silane coupling agent. Such free radical reactions and conditions suitable for performing them will be readily selected by the person of ordinary skill in the art, given the benefit of this disclosure.

As mentioned above, curatives used in forming the present compositions may include peroxides, amine curatives and polyhydroxy (e.g., bisphenol) curatives. In general, the curative may be used in amounts of from about 0.5-5 parts by weight per hundred parts by weight resin (phr).

Example peroxide curatives may include tert-butylcumyl peroxide (e.g., Trigonox® T), 2,5-dimethyl-2,5-di(t-butylperoxy)hexyne-3,2,5-dimethyl-2,5-di-(tert-butylperoxy)hexane (e.g., Trigonox® 101), alpha, alpha-bis(tert-butylperoxy-isopropyl)benzene (Perkadox® 14/40 and Perkadox® 14 (without carrier)), and 2,5-dimethyl-2,5-di(t-butyl-peroxy) hexane (Varox.® DBPH-50 or Varox® DBPH (liquid form)).

A co-agent may be used in combination with the peroxide curative. Some co-agents for peroxide curing of fluoroelastomers include, but are not limited to, triallylisocyanurate (TAIC), trimethallylisocyanurate (TMAIC) and triallylcyanurate (TAC), triacrylformal, triallyl trimellitate, N,N'-m-phenylenebismaleimide, diallyl phthalate, tetrallylterephthalamide, tris(diallylamine)-s-triazine, triallyl phosphate, N,N,N',N'-tetrallyl-malonamide; trivinyl-isocyanurate; 2,4, 6-trivinyl-methyltrisiloxane; N,N'bisallylbicyclo-oct-7-ene-disuccinimide (BOSA), and N,N-diallylacrylamide. Generally, the co-agent may be used in an amount of 0.1 to 10 parts by weight per 100 parts by weight of resin.

Examples of amine curatives are organic aliphatic or aromatic diamines such as ethylenediamine or hexamethylenediamine, or their carbamates, hydrochlorides, oxalates, or reaction products with hydroquinone. Specific examples include hexamethylene diamine carbamate, such as DIAK (trademark of DuPont Dow Elastomers) no. 1, dicinnamylidene diamine carbamate, such as DIAK no. 3, and 4,4'-bis(aminocyclohexyl)-methane carbamate, such as DIAK no. 4. Examples of bisphenol curatives are fluorinated bisphenol A, 4,4'-hexafluoroisopropylidene diphenol (i.e., bisphenol AF) and derivatives thereof. Other polyhydroxy compounds may also be used.

Figure 4:
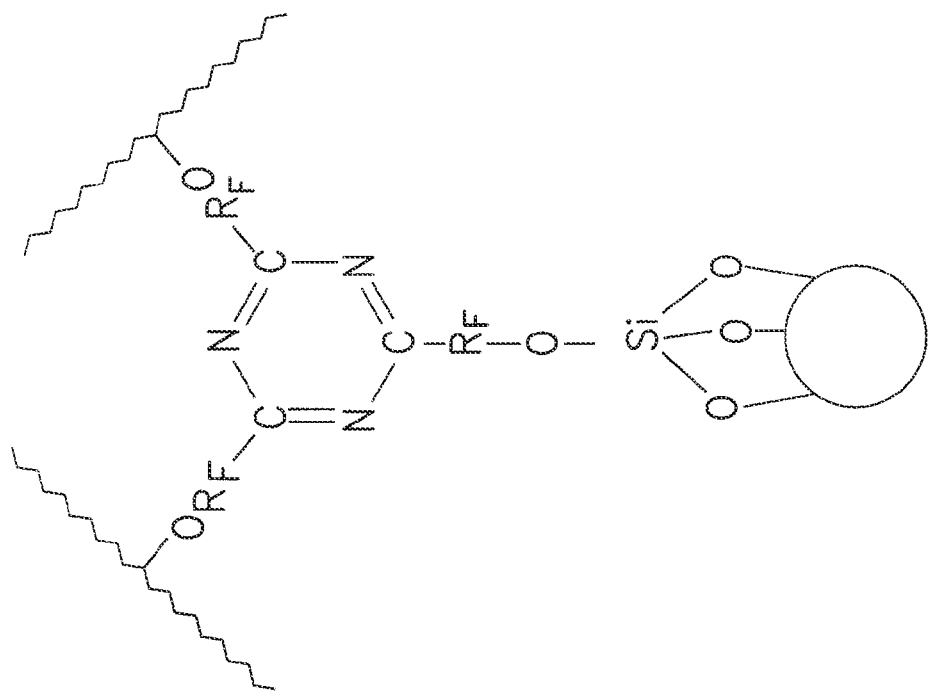
FIG. 4 is an illustration of a thermally induced cure mechanism between a polymer and a silane coupling agent covalently coupled to a filler particle.
Figure 4:
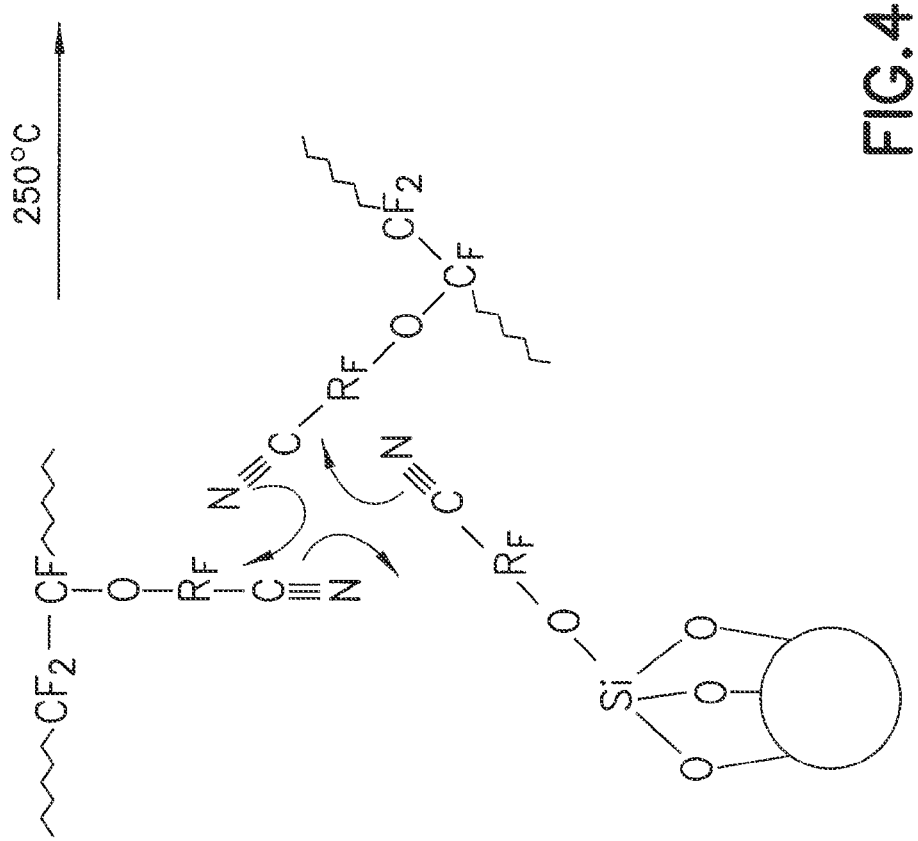

In some instances, the compositions may be cured without the addition of a curative, but by thermal curing. For example, crosslinking may be thermally induced in nitrile-containing elastomers by formation of a triazine ring, between nitriles in the polymer and/or present within the Q group of a silane coupling agent, as illustrated in FIG. 4.

Additional components may be used in or with the polymer-silane coupling agent-filler composition. For examples, additives, viscosity modifiers, processing aids and the like may be used. Examples of such additional components include, but are not limited to, antiozonants, antioxidants, plasticizers, resins, flame retardants, lubricants, one or more curing agents such as, for example, sulfur, sulfur donors, activators, accelerators, peroxides, thickeners, thinners, solvents, salts and other materials.

In processing the materials, various devices such as mills, mixers, molds, calendering devices, extruders and the like may be used. For example, the materials may be blended, open milled, mixed with an internal mixer (which may include temperature control to avoid scorching) or otherwise combined in a suitable device. One pass or multi-pass mixing may be used. High shear mixing may be used to obtain good dispersion. The materials may be reworked in one or more additional stages to further assist in mixing. Illustrative molding processes that may be used with the materials include, but are not limited to compression, transfer and injection molding, extrusion and calendering. In compression molding, a preform may be used to provide a desired shape or mass to the resulting material. In injection molding, the material may be injected at high pressure into a mold. Calendering may be used to produce sheets of material. The compounds for calendaring may be used with viscosity modifiers to provide medium or low viscosity materials to facilitate the calendaring process. The materials may also be shaped by extrusion. For example, the material may be forced through a shaping die below a curing temperature to impart a desired shape. Release agents may be used in the preforms, molds and other parts to facilitate removal of the compressed or produced material from these devices.

Figure 5C:
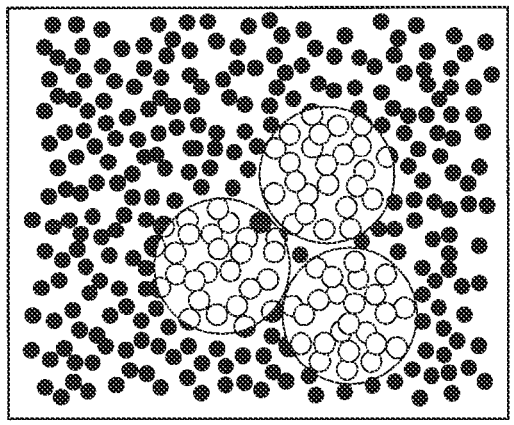
FIGS. 5A-5C are illustrations showing particle dispersions and phases, in accordance with certain examples.
Figure 5B:
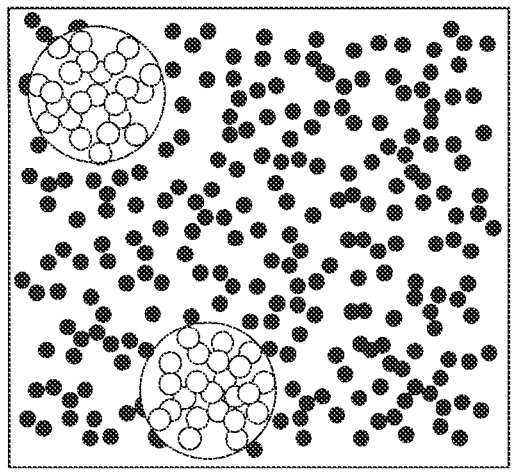
Figure 5A:
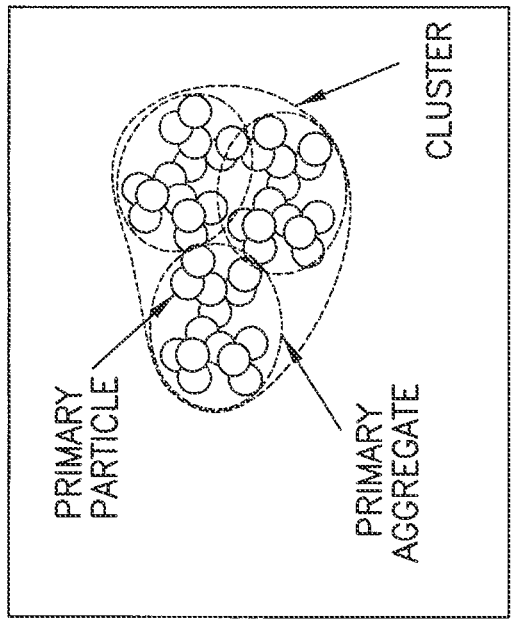

The presence of a silane on the surface of the filler can have a great effect on the filler dispersion and resulting mechanical properties of the composition. FIGS. 5A, B and C are schematic views of a polymer filled with the thermally stable silane coupling agent modified silica at different filler concentrations. FIG. 5A shows the local structure of one cluster formed by primary silica aggregates. FIG. 5B shows aggregated filler clusters below the gel point $\Phi^*$, and FIG. 5C shows aggregated filler clusters above the gel point $\Phi^*$. By modifying the surface of the filler with a silane, and subsequent coupling to a polymer through the silane, a reduction in the Payne effect (also known as the Fletcher-Gent effect) may be achieved. The Payne effect is the non-linearity appearing at small strains (a few tens to a few % strain) due to breakage of the filler three-dimensional network. When the strain is removed or reduced back to the original level, the network reforms and this process generates a hysteresis. The hysteresis generates heat that can be detrimental to the component lifetime. Adding a silane coupling agent to the filler surface and covalently coupling the modified filler to the polymer can reduce this hysteresis and therefore energy dissipation, which in turn can increase the overall use life of the part or component that is produced from the material.

In certain examples, the compositions disclosed herein may be used in downhole tools and devices such as packers used in extraction of fuels through a wellbore. For example, downhole tools, such as modular wireline tools or drilling tools with evaluation capabilities, that employ probes for engaging the formation and establishing fluid communication may be used to make the pressure measurements and acquire the fluid samples. Fluid in general is drawn into the downhole tool through an inlet in the probe. In some instances, such as for tight, low permeability, formations, sampling probes are often replaced by dual inflatable packer assemblies. Examples of such probe and packer systems are depicted, for example, in U.S. Pat. Nos. 7,392,851, 7,363,970, 7,331,581, 6,186,227, 4,936,139, 4,860,581 and 4,660,637 and assigned to Schlumberger, the entire contents of which are hereby incorporated herein by reference for all purposes. In one configuration, a packer comprises, for example, a resilient element, a housing and a rupture disk. The resilient element is adapted to seal off an annulus of the well when compressed, and the housing is adapted to compress the resilient element in response to a pressure exerted by fluid of the annulus on a piston head of the housing. The housing includes a port for establishing fluid communication with the annulus. The rupture disk is adapted to prevent the fluid in the annulus from entering the port and contacting the piston head until the pressure exerted by the fluid exceeds a predefined threshold and ruptures the rupture disk. In another configuration, dual packer elements may be used with either or both of the packer elements comprising one or more of the materials described herein. For example, packer elements may be spaced apart along a downhole tool conveyed by a wireline in a borehole penetrating a subsurface formation. Although a wireline tool is illustrated, other downhole tools conveyed by drill string, coiled tubing, etc., are also suited for such tasks. When inflated, the packer elements cooperate to seal or isolate a section of the borehole wall, thereby providing a flow area with which to induce fluid flow from the surrounding formation(s). Other packers and elements of packer assemblies may be produced using one or more of the compositions described herein. In one embodiment, the compositions may be used in a swellable packer for open-hole zonal isolation. For example, a fluoroelastomer composition as described herein can be used as the barrier coating for swellable materials to slow down the rate of swelling.

Figures 6, 7:
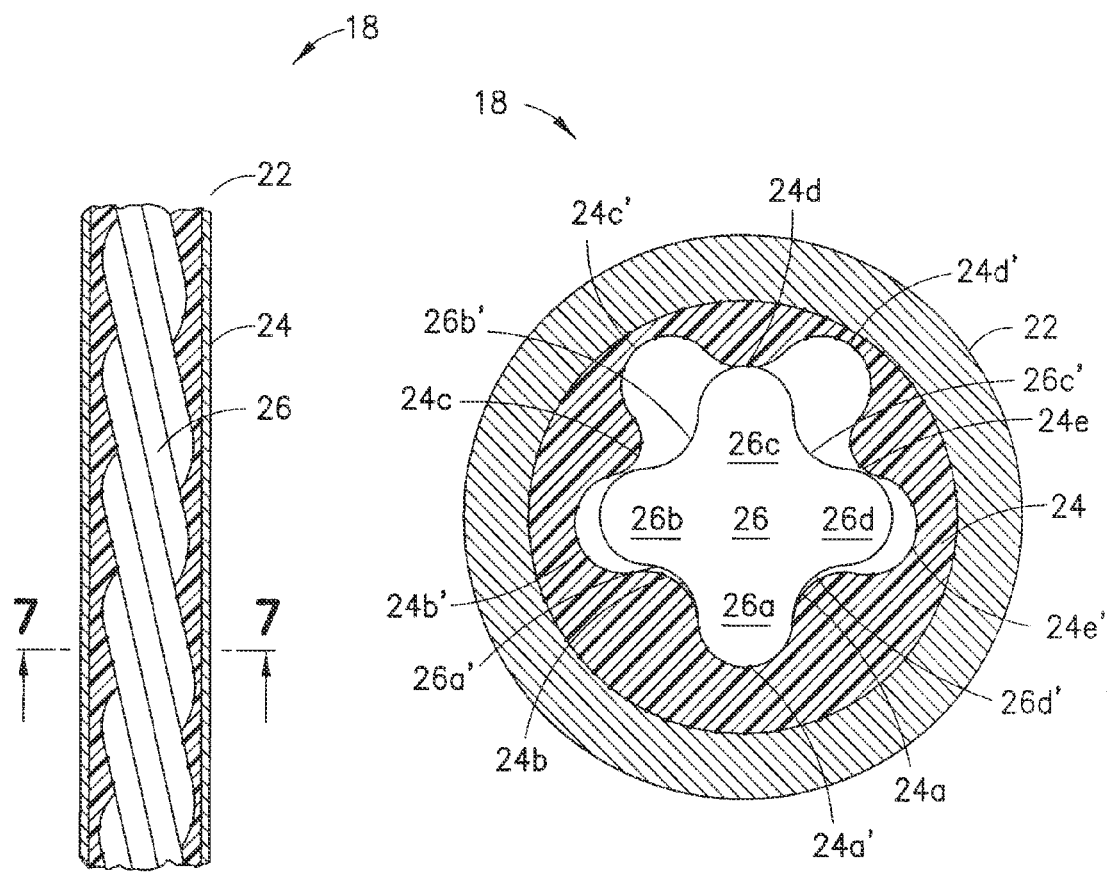
FIG. 6 shows a detailed view of a power section of a downhole motor.
FIG. 7 is a cross-sectional view of the power section of the downhole motor, taken along section line 7-7 of FIG. 6

In certain embodiments, the compositions disclosed herein may be used to coat one or more devices such as, for example, a coating on the stator or rotor of a mud motor. For example, the composition may be used in a motor that imparts rotational drive to a drilling assembly. Illustrative mud motors and assemblies using them are described, for example in commonly assigned U.S. Pat. Nos. 7,289,285, 6,419,014, 5,727,641, 5,617,926, 5,311,952, the entire disclosure of each of which is hereby incorporated herein by reference for all purposes. Referring now to FIGS. 6 and 7, an example mud motor using compositions of the present disclosure is shown.

FIGS. 6 and 7 show details of the power section 18 of a conventional downhole motor. The power section 18 generally includes a tubular housing 22 which houses a motor stator 24 within which a motor rotor 26 is rotationally mounted. The power section 18 converts hydraulic energy into rotational energy by reverse application of the Moineau pump principle. The stator 24 has a plurality of helical lobes, 24a-24e, which define a corresponding number of helical cavities, 24a'-24e'. The rotor 26 has a plurality of lobes, 26a-26d, which number one fewer than the number of stator lobes and which define a corresponding plurality of helical cavities 26a'-26d'. In accordance with embodiments, the stator 24 and/or rotor 26 are formed of an elastomeric material having a composition of the present disclosure that provides the lobe structure of the stator and/or rotor. The rotor and stator are dimensioned to form a tight fit (i.e., very small gaps or positive interference) under expected operating conditions, as shown in FIG. 6. Other embodiments may use an elastomeric rotor. The rotor 26 and stator 24 form continuous seals along their matching contact points which define a number of progressive helical cavities. When drilling fluid (mud) is forced through these cavities, it causes the rotor 26 to rotate relative to the stator 24. During drilling, the mud motor elastomers in general experience severe mechanical stress and deformation (mainly dynamic), aggressive downhole fluids, and high temperature and high pressure. The compositions of the present disclosure may possess silanes (and derived crosslinks) having an improved thermal stability so that reinforcing effect of the fillers will be present even at high temperatures (e.g., temperatures greater than 150° C., which is considered the upper limit for conventional elastomers used in mud motors).

In certain examples, the compositions described herein may be used in a formation tester such as MDT (Modular Formation Dynamics Tester) from Schlumberger, permeability probes, power drive pads and other components and tools commonly used downhole for oilfield and gas exploration.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications and alterations of the disclosed illustrative aspects, examples and embodiments are possible.

What is claimed is:

1. A composition suitable for use in high temperature downhole environments greater than 150° C. comprising a fluoropolymer covalently coupled to a filler through a thermally stable silane coupling agent, the fluoropolymer comprising a cure site monomer incorporated therein, wherein the silane coupling agent is bonded to the cure site monomer of the fluropolymer and wherein the silane coupling agent has a chemically identical reactive moiety to the cure site monomer and wherein the filler is surface treated with the silane coupling agent; and the cure site monomer is selected from one of bromine-containing olefins, bromine-containing vinyl ethers, iodine-containing olefins, iodine-containing vinyl ethers, fluorine-containing olefins having a nitrile group, fluorine-containing vinyl ethers having a nitrile group, and non-conjugated dienes.

2. The composition of claim 1, in which the fluoropolymer is synthesized using monomers selected from the group consisting of vinylidene fluoride (VDF), tetrafluoroethylene (TFE), hexafluoropropylene (HFP), chlorotrifluoroethylene (CTFE), and a perfluoro(alkylvinyl ether) (PAVE).

3. The composition of claim 2, in which the filler is selected from the group consisting of precipitated silica, amorphous silica, vitreous silica, fumed silica, fused silica, quartz, glass, aluminum, aluminum-silicate, copper, tin, talc, inorganic oxides, steel, iron, asbestos, nickel, zinc, silver, lead, marble, chalk, gypsum, barites, graphite, carbon black, and treated carbon black.

4. The composition of claim 1, wherein the silane coupling agent has the formula $Q_m$-Si—$Z_n$, where Q comprises one or more groups that can provide covalent attachment to the polymer, Z comprises one or more groups that can provide covalent attachment to the filler, and the sum of m+n is equal to four.

5. The composition of claim 4, wherein Q is —R"-G or —CR'$_2$—CR'—R"-G, where R' is a hydrogen or a fluorine, R" is a linear or branched $C_1$-$C_{18}$ alkyl group, optionally containing one or more ether oxygen atoms and optionally fluorinated, and G is a halogen, a nitrile group, or a vinyl group.

6. The composition of claim 1, in which all of the reactive sites of the filler are covalently coupled to the silane coupling agent.

7. The composition of claim 1, wherein the silane coupling agent has chemically identical reactive moiety as the pendant group of the cure site monomer.

8. A moving or progressive cavity motor or pump assembly having an inlet end and an outlet end for use in a downhole environment, the motor or pump comprising:
a housing;
a rotor and a stator disposed within the housing, wherein a surface of the rotor or the stator is made of an elastomer material to permit a seal to form between contacting surfaces of the rotor and the stator; wherein the elastomer material comprises a fluoropolymer covalently coupled to a filler through a thermally stable silane coupling agent, wherein the silane coupling agent is bonded to a cure site moiety of the fluropolymer and wherein the silane coupling agent has a chemically identical reactive moiety to a cure site moiety of the fluoropolymer and wherein the filler is surface treated with the silane coupling agent.

9. The motor or pump of claim 8, in which the polymer is a fluoropolymer synthesized using monomers selected from the group consisting of vinylidene fluoride (VDF), tetrafluoroethylene (TFE), hexafluoropropylene (HFP), chlorotrifluoroethylene (CTFE), and a perfluoro(alkylvinyl ether) (PAVE).

10. The motor or pump of claim 9, in which the filler is selected from the group consisting of precipitated silica, amorphous silica, vitreous silica, fumed silica, fused silica, quartz, glass, aluminum, aluminum-silicate, copper, tin, talc, inorganic oxides, steel, iron, asbestos, nickel, zinc, silver, lead, marble, chalk, gypsum, barites, graphite, carbon black, and treated carbon black.

11. The motor or pump of claim 8, wherein the silane coupling agent has the formula $Q_m$-Si—$Z_n$, where Q comprises one or more groups that can provide covalent attachment to the polymer, Z comprises one or more groups that can provide covalent attachment to the filler, and the sum of m+n is equal to four.

12. The motor or pump of claim 11, wherein Q is —R"-G or —CR'$_2$—CR'—R"-G, where R' is a hydrogen or a fluorine, R" is a linear or branched $C_1$-$C_{18}$ alkyl group, optionally containing one or more ether oxygen atoms and optionally fluorinated, and G is a halogen, a nitrile group, or a vinyl group.

13. The motor or pump of claim 8, wherein the fluoropolymer comprises a cure site monomer incorporated therein.

14. The motor or pump of claim 13, wherein the silane coupling agent has chemically identical reactive moiety as the pendant group of the cure site monomer.

15. The motor or pump of claim 13, wherein the cure site monomer is selected from one of bromine-containing olefins, bromine-containing vinyl ethers, iodine-containing olefins, iodine-containing vinyl ethers, fluorine-containing olefins having a nitrile group, fluorine-containing vinyl ethers having a nitrile group, and non-conjugated dienes.

* * * * *